United States Patent [19]
Schulz et al.

[11] Patent Number: 5,513,006
[45] Date of Patent: Apr. 30, 1996

[54] PHOTO-THERMAL SENSOR INCLUDING AN EXPANSION LENS IN A LIGHT BEAM PATH THROUGH A SAMPLE FOR DETERMINING THE CONCENTRATION OF A COMPOUND IN THE SAMPLE

[75] Inventors: Torsten Schulz, Karlsruhe; Werner Faubel, Eggenstein-L., both of Germany

[73] Assignee: Kernforschungszentrum Karlsruhe GmbH, Karlsruhe, Germany

[21] Appl. No.: 378,566

[22] Filed: Jan. 26, 1995

[63] Related U.S. Data continuation-in-part of PCT/DE93/00507, June 11, 1993

[30] Foreign Application Priority Data

Sep. 18, 1992 [DE] Germany ............... 42 31 214.0

[51] Int. Cl.$^6$ ................................. G01N 21/00
[52] U.S. Cl. ......................................... 356/432
[58] Field of Search ...................... 356/432, 432 T

[56] References Cited

U.S. PATENT DOCUMENTS

| | | | |
|---|---|---|---|
| 4,750,822 | 6/1988 | Rosencwaig et al. | 356/432 |
| 4,795,260 | 1/1989 | Schuur et al. | 356/432 T |
| 4,938,593 | 7/1990 | Morris et al. | 356/432 T |
| 5,365,065 | 11/1994 | Power | 356/432 |

FOREIGN PATENT DOCUMENTS 0427943  5/1991  European Pat. Off. .

OTHER PUBLICATIONS

Xu et al, "Thermal Lens–Circular Dichroism Spectropolarimeter", Applied Spectroscopy, vol. 44, No. 6, 1990, pp. 962–966.

Dual Beam Optic Fiber Lens Spectroscopy, D. Rojas, R. Silva, D. Spear R. Russo; Anal. Chem. 1991, 63, 1927–1932.

Comparison of BaTiO$_3$ Optical Novelty Filter and Photothermal Lensing Config. in Photothermal Experiments Anal. Chemistry 64 (1992) Sep. 1, No. 17, Washington D.C.

Pulsed Mode Thermal Lens effect Detection in the near field via thermally induced probe beam spatial phase modulation: a theory Applied Optics/vol. 29, No. 1/1. Jan. 1990 pp. 52–62, J. F. Power.

Mode Mismatched Laser Induced Thermal Lens effect detection via spatial Fourier Analysis of Beam—J. F. Powes and E. D. Salin Anal. Chem. 1988, 60, 838–842.

*Primary Examiner*—Frank Gonzalez
*Assistant Examiner*—Jason D. Eisenberg
*Attorney, Agent, or Firm*—Klaus J. Bach

[57] ABSTRACT

In a photo-thermal sensor for determining the concentration of a compound in a sample which includes an excitation light source generating a first light beam of a wave length which is well absorbed by the compound to be determined, a modulator and an optical lens system disposed in the first light beam such that the first light beam is constricted at the location of the sample through which it is directed, a probe light source generating a second light beam extending at a right angle to the first light beam, a beam divider arranged at the intersection of the first and second light beams whereby part of the first light beam is deflected at one side of the beam divider and the second light beam passes through the beam divider such that both beams incide on the sample anti a photo-sensitive detector arranged in the light beam path behind the sample, a diaphragm is arranged in the beam path directly after the sample and an expansion lens adapted to expand the second light beam at the location of the sample to a diameter at least 5 times the diameter of the first light beam is disposed in the path of the second beam ahead of the beam divider for determining the loss of strength of the second light beam reaching the detector after passage through the sample and the diaphragm as an indication of the concentration of the compound in the sample.

11 Claims, 5 Drawing Sheets

PHOTO-THERMAL SENSOR INCLUDING AN EXPANSION LENS IN A LIGHT BEAM PATH THROUGH A SAMPLE FOR DETERMINING THE CONCENTRATION OF A COMPOUND IN THE SAMPLE

This is a continuation-in-part application of International application PCT/DE93/00507 filed Jun. 11, 1993 and claiming the priority of German application P 42 31 214.0 of Jun. 18, 1992.

BACKGROUND OF THE INVENTION

The invention relates to a photo-thermal sensor for determining the concentration of a compound in a material sample.

To determine the concentration of a compound in a material sample, the sample is irradiated by light. If the ample contains a compound which absorbs the light, light energy is converted into heat energy, whereby the temperature of the sample rises. Since the refraction index of a material generally rises with the temperature, an optical medium corresponding to a gradient index lens is formed thereby, which is defined as a "thermal lens" T.L.). The presence of a thermal lens can be detected by directing a second light beam onto the sample and determining its refraction. The sample needs to be sufficiently transparent so that the second light beam can be detected after passage through the sample.

A photo-thermal sensor of this type is disclosed in a publication by Dorys Rojas, Robert J. Silva, Jonathan D. Spear and Richard E. Russo in Anal. Chem. 1991, 63, 1927–1932. With the sensor described therein the concentration of samples consisting of an aqueous solution of $Nd^{+3}$-ions in a cuvette is determined.

As excitation light source a color laser is utilized which emits a coherent light of a wave length of 590 nm and which is pumped by an argon ion laser. The light beam of the excitation light source is modulated by 10 Hz and is guided by means of a light conductor and by means of a chromatic optical arrangement comprising three lenses in such a way that at the sample location the beam is constricted. As probe laser beam a helium-neon laser beam is utilized whose coherent light beam extends in a direction normal to that of the excitation laser and is guided in an additional lens in such a way that a second constriction is formed in the beam after passage through the sample. The light of the excitation light source is deflected on a beam divider in the direction toward the sample. A part of 50% of the light which passes through the beam divider is directed to a first detector. The excitation laser beam passes through the beam divider and also strikes the sample. In the path of the light beam which passes through the sample there is arranged first an interference filter and then a second light conductor at which most of the light is diaphragmed out. Following this arrangement there is a second detector and an analyzing unit.

As is apparent from this publication the distance between the sample and the entry surface of the second light conductor must be at least 10–15 cm in order to provide for sufficient light intensity modulation to the second detector. Consequently such a photo-thermal sensor cannot be of very compact design.

Another sensor for the photo-thermal spectroscopy is known from DE 39 37 905 Cl. In this sensor, a sample light beam and a modulated excitation light beam are coupled into a light conductive fiber. At the end of the optical fiber, sample light beam and excitation light beam emerge and are focused in a chromatic lens arrangement. For this purpose a chromatic lens arrangement is utilized in which the two light beams have spatially distinct focal points. The medium to be analyzed is disposed in the area of the focal points. The intensity of the probe light beam is recorded by the detector by way of an apertured diaphragm. The detector signal is supplied to a central analyzing unit.

The use of a wave-length dependent lens arrangement in the particular sensor results in a limited choice of wave length combinations for the excitation light source and the probe laser. Because of the particular characteristics of representation of the optical fiber such a sensor is not particularly sensitive.

A further photo-thermal sensor is known from a publication of Shaole Wu and Norman J. Dovichi entitled "Fresnel diffraction theory for steady-state thermal lens measurements in thin films", J. Appl. Phys. 67(3) (1. Feb. 1990) pages 1170–1182. In this sensor, excitation light source and probe laser light source are the same. For signal optimization the Fresnel infraction laws are applied.

It is the object of the present invention to provide a photo-thermal sensor which is very compact. Particularly, the distance between the sample and the arrangement where most of the light passing through the sample is diaphragmed out is reduced without a loss of sensitivity with respect to the change of the refraction index.

SUMMARY OF THE INVENTION

In a photo-thermal sensor for determining the concentration of a compound in a sample which includes an excitation light source generating a first light beam of a wave length which is well absorbed by the compound to be determined, a modulator and an optical lens system disposed in the first light beam such that the first light beam is constricted at the location of the sample through which it is directed, a probe light source generating a second light beam extending at a right angle to the first light beam, a beam divider arranged at the intersection of the first and second light beams whereby part of the first light beam is deflected at one side of the beam divider and the second light beam passes through the beam divider such that both beams incide on said sample and a photo-sensitive detector arranged in the light beam path behind the sample, a diaphragm is arranged in the beam path directly after the sample and an expansion lens adapted to expand the second light beam at the location of the sample to a diameter at least 5 times the diameter of the first light beam is disposed in the path of the second beam ahead of the beam divider for determining the loss of strength of the second light beam reaching the detector after passage through the sample and the diaphragm as an indication of the concentration of the compound in the sample.

The publication by J. F. Powers entitled "pulsed mode thermal lens effect detection in the near field via thermally induced probe beam spatial phase modulation: a theory", Applied Optics, Vol. 29, No. 1, Jan. 1, 1990, pages 52–63, develops a theory for the thermal lens utilizing the Fresnel refraction laws based on the following limiting conditions:

(i) A focused excitation light source is used in order to demonstrate the photo-thermal effect by way of the refraction index gradient (see FIG. 1).

(ii) A coherent probe laser beam is used to detect the refraction index gradient profile.

(iii) Excitation and probe light beams are guided in a collinear manner.

(iv) The radii ratio of stimulation and detection light beams is variable in the range of between 1:2 and 1:10 (see FIG. 2).

(v) The distance d between the probe and the aperture diaphragm can be between 0.5 and 200 cm.

(vi) For signal improvement, the Fresnel refraction laws are utilized.

The photo-thermal sensor according to the invention however is different from the photo-thermal system proposed by J. F. Powers in some essential ways:

(i) In accordance with the above publication the excitation light source needs to be pulsed. This is not necessary with the arrangement according to the invention.

(ii) It is not indicated in the above publication how the excitation light beam is to be guided after passage through the sample.

(iii) According to the theory presented in the above publication the thickness 1 of the sample is subject to limiting conditions (l<<d). Consequently the sample has to have a thickness of only a small fraction of the distance between the sample and the diaphragm. Such limits are not existent with the arrangement according to the invention.

(iv) The light beam emitted from the probe laser source needs to be focused ahead of the sample in accordance with the above theory. In accordance with the arrangement of the invention the light beam only needs to be expanded.

(v) The theory developed in the above publication relates to a space resolution detection method with an array of diodes as a detector. In this case the array of diodes takes the place of the diaphragm.

An essential feature of the photo-thermal sensor according to the invention resides in the fact that, in the beam path of the probe laser, there is no collection lens or photoconductor which would constrict the light beam at a location past the sample but that there is an expansion lens. This lens expands the light beam in a cone-like fashion such that the probe light beam radius at the location of the sample is at least five and up to fifty times the radius of the light beam coming from the excitation light source which is constricted at the sample location.

In contrast to the sensor known from the publication discussed earlier, in the arrangement according to the invention the diaphragm is arranged right after the sample without loss of sensitivity with regard to changes in the fraction index. This results in a highly advantageous arrangement since the reproduction optical system, the lens, the beam divider, the sample, possibly the iris diaphragm and the aperture diaphragm can all be integrated in a compact building component.

The size of the expansion of the light beam emitted from the probe laser depends on the geometrical extent of the sample and on the required sensitivity of the sensors with respect to a change in the refraction index. The expanded beam is to encompass the whole sample. The lower limit for the expansion is selected, for example, if, as with liquid samples, only a small volume is available such that only a small surface area can be utilized. The selection of yet smaller expansion generally results in reduced sensitivity. If larger samples are available a larger expansion is preferred since this improves the sensitivity of the sensor. With very large samples a light beam which has been expanded to more than fifty times may even be utilized.

The light beam from the excitation light source should be constricted at the location of the sample or at least nearby in such a way that the full light intensity is concentrated on the sample. As excitation light source, for example, a laser, a laser diode, or an arc lamp may be used. The light of such a light source does not need to be coherent.

The photo-thermal sensor according to the invention is preferably provided with an achromatic optical system. Then, it is not subject to limits with regard to the selection of the wave length of the excitation and the probe light and can be utilized as a real spectrometer if a fully adjustable laser is utilized as the excitation light source.

As beam divider preferably long or short wave pass filters are employed since a higher light intensity can be directed onto the sample with such filters. Through the long or short wave pass filter the first as well as the second light beam are collinearly and centro-symetrically coupled and beamed into the sample. In order to achieve this, in a first embodiment in which the first light beam is deflected and the second light beam is transmitted, long or short wave pass filters are utilized whose maximum reflection capability is at the wave length of the excitation light and whose maximum transmission capability is at the wave length of the probe light. In a second embodiment, wherein the positions of excitation light source and probe laser are reversed, also the reflection and transmission behavior of the long pass edge filter must be switched accordingly.

Particularly preferred is a photo-thermal sensor which has an iris diaphragm arranged in the beam path between the beam divider and the sample. The free diameter of the iris diaphragm when fully open should be so large that both light beams can pass without inhibition. With closed diaphragm the open diameter may be, for example, 0.5 mm. The iris diaphragm may be used in combination with the aperture diaphragm as an adjustment aid for the long pass edge filter. Only when both light beams pass through the closed iris diaphragm and the aperture diaphragm, the condition for collinear centro-symmetrical coupling are guaranteed. For measuring the photo-thermal effects the iris diaphragm is opened.

Although a simple aperture diaphragm is preferred other diaphragms may be utilized in its place. The opening of the aperture diaphragm is so selected that the first light beam, that is, the beam emitted from the excitation light source, passes through the diaphragm without being inhibited. The opening diameter is, for example, 1 mm. Of the second light beam emitted by the probe laser, only the beam center is transmitted.

The diaphragm is arranged in the beam path preferably ahead of the filter and directly behind the sample. In this manner a Fresnel-refraction pattern of the second light beam emitted from the probe laser is depicted. The diaphragm can be arranged in this manner because the second light beam which is emitted from the probe laser is expanded by the expansion lens. Comparing the arrangement with that disclosed in the earlier discussed publication by D. Rojas et al. it is noted that the uncoupling of the first beam which is emitted from the excitation light source is omitted. In the sensor arrangement described in this publication the filter is disposed between the sample and the diaphragm. If one would chose such an arrangement with a small distance (<10 cm) between sample and diaphragm, interference effects resulting from back reflections of the first light beam into the sample and the formation of a further undesired photo-thermal effect would be unavoidable. Also for this reason, it is necessary to maintain a large distance between the sample and the diaphragm in the arrangement described in the publication.

The application and utilization of the Fresnel-refraction permits the use of very small detectors without loss of sensitivity; furthermore, the photo-thermal sensor according to the invention is easy and simple to operate.

In the beam path between the sample and the second detector there is disposed a filter which is preferably another long pass edge filter by which most of the excitation and probe light is diaphragmed out. The light so eliminated may be directed into a beam stop. But in place of a beam stop there may be provided a third detector by which direct absorption measurements can be performed. With the use of a long or short wave pass filter, back reflections into the sample are furthermore reliably prevented.

With the photo-thermal sensor according to the invention gaseous, liquid and solid samples can be examined. Liquid and gaseous samples can be stationary or flowing samples, that is, the sensor according to the invention is also usable as a flow sensor. Preferably the frequency of the modulator is adapted to the type of sample: With stationary liquid samples a frequency of 5 Hz has been found to be suitable. For moving samples the modulator frequency should be in the range of 40 to 60 Hz. Even higher frequencies are utilized for examining solid samples; there, the frequency may be about 3000 Hz.

With the photo-thermal sensor according to the invention refraction index differences of $<10^{-8}$ and consequently extinctions of $10^{-6}$ to $10^{-5}/cm^{-1}$ can be determined.

With such a sensitivity, the sensor according to the invention is well suitable for analytical applications particularly for drinking water analysis since already ppb-amounts of organic poisons can be detected.

By the use of an expansion lens as proposed by the invention the detection limits with regard to the sensors of the earlier-described type are substantially lowered.

As sensors based on the concept of the present invention are very compact and the distance over which the two beams have to be collinear is very small, the detection signal is relatively insensitive with regard to a spacial displacement of the two beams relative to one another.

Furthermore, the large expansion of the probe beam results in a similar insensitivity. With a slight displacement of this beam, the diaphragm opening is still essentially in the center of the beam. It has to be taken into consideration that the probe laser beam intensity at the aperture diaphragm (that is, at the probe laser intensity maximum) changes only very little. For the adjustment to the apparatus it is therefore not necessary to bring the two laser beams into exact collinear alignment; there is some tolerance.

Embodiments of the photo-thermal sensor according to the invention will be described below in greater detail on the basis of figures and examples.

DESCRIPTION OF THE PREFERRED EMBODIMENT

Figure 1:
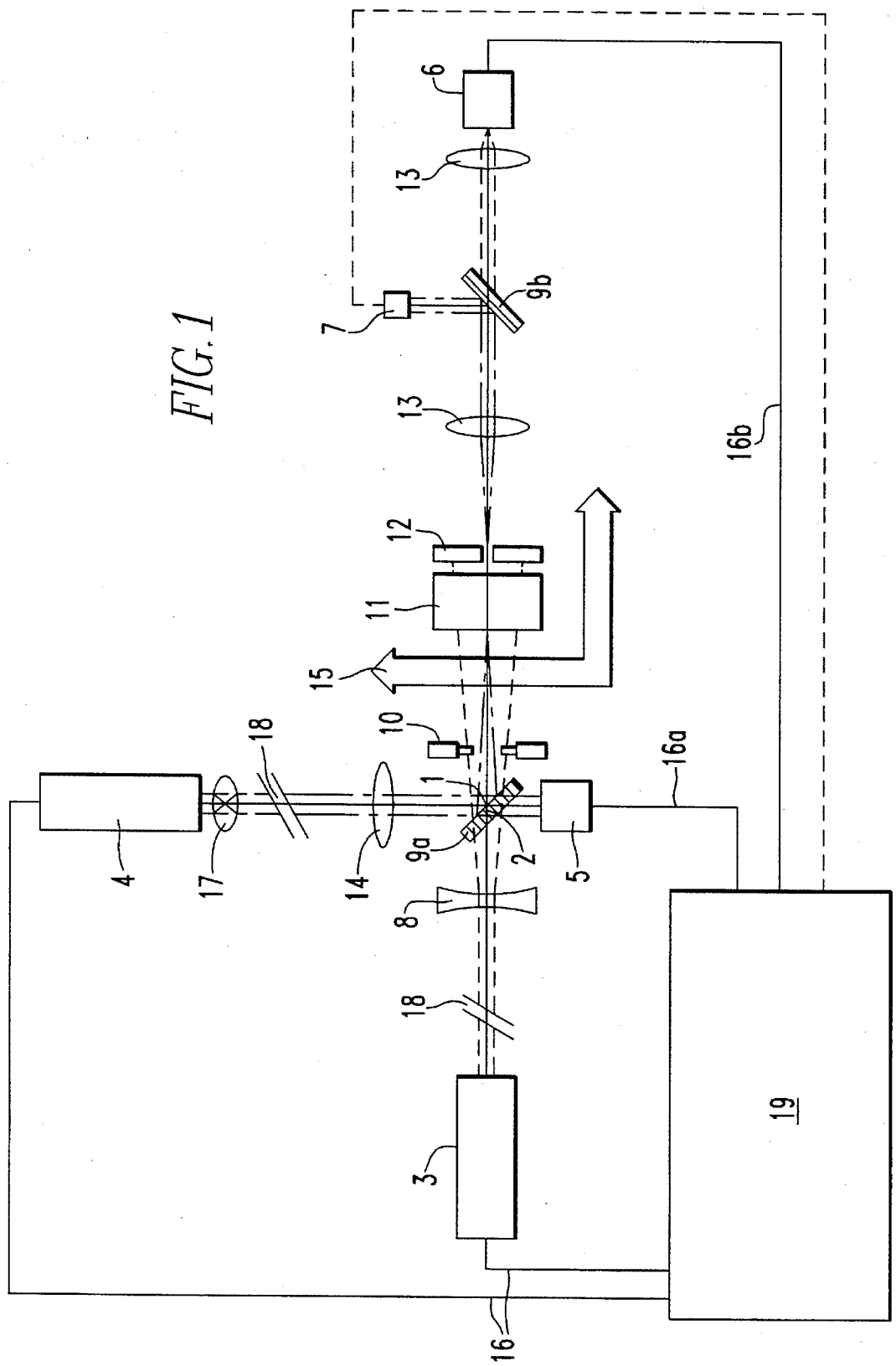
FIG. 1 shows an embodiment of a photo-thermal sensor according to the invention.

FIG. 1 shows an embodiment of the photo-thermal sensor according to the invention wherein an excitation light source 4 consisting of an argon ion laser with a power of 150 mW emits a first laser light beam with an excitation wave length of 364 nm. At this wave length an aqueous solution of DNOC has an absorption maximum. The laser beam is chopped by a modulator 17 at a frequency of 5.2 Hz and directed to an achromatic optical lens system 14 for converging in the sample 11. The achromatic optical system 14 has a focus length of $f_{achromatic}=200$ mm and generates in the sample a contraction of the laser beam (focusing point) with a diameter of 250 μm.

As probe light source 3, a He-Ne-laser providing a light beam with a wave length of 633 nm is utilized. At this wave length, an aqueous solution of DNOC has an absorption minimum. The second (probe) laser light beam extends at an angle of 90° with regard to the first light beam and is passed through an expansion lens 8 with a focal length of $f_{633nm}=$ 20 nm. The expansion lens 8 is arranged in the beam path 125 mm in front of the sample 11 whereby the beam is widened at the sample 11 location to a diameter of 5 mm. As samples aqueous solutions of DNOC selectively in 20 mm and 10 mm long test cells (flow bulbs) are utilized.

The two laser beams are coupled by the long-pass edge filter 9a in a centro-symmetrical and collinear manner and are together directed onto the sample 11. The light beam originating from the excitation light source 4 is reflected on the upper side 1 of the filter 9a. The light beam originating from the probe light source 3 reaches the filter 9a at its second, lower side 2 and passes through the filter. The long or short wave pass filter 9a has a maximum reflection capability of 99.5% at the wave length of the excitation light source 4 and a maximum transmission capability of 99.5% at the wave length of the probe light source 3 at normal polarization orientation (S-pole).

Ahead of the sample 11, there is provided an iris diaphragm 10 with a clear opening of 0.5 mm when it is fully closed. The iris diaphragm 10 serves, together with the aperture diaphragm 12, as an adjustment aid for the filter 9a and the sample 11.

The sample is mounted of a position-adjustable structure 15 shown schematically by an angled arrow so that the sample can be moved in a plane normal to the two laser beams and be properly positioned in the beam path. Furthermore the sample 11 can be tilted normal to the two beams so that any beam displacement (caused by different refraction of the two beams at the interface air/sample as a result of the wave length dispersion of the light) can be accommodated and the collinearity can be maintained.

Directly behind the sample 11, at a distance of 5 mm therefrom, there is the aperture diaphragm 12. The opening diameter of the aperture diaphragm of 1 mm is so selected that the first light beam from the excitation light source 4 passes without being inhibited, whereas, of the second light beam from the probe light source 3, only the beam center is transmitted. This insures that, at the detector 6, the largest intensity changes generated by the thermal lens in the plane of the aperture diaphragm 12 can be detected.

The optical system 13 insures optimal light stimulation of the detector 6 by the light beam emitted by the probe light source 3. The additional long or short wave pass filter 9b deflects the first light beam coming from the excitation light source 4 and directs it into a beam stop 7. In this manner, back reflections of the first light beam emitted from the excitation light source 4 into the sample, which would lead there to undesirable additional thermal effects, are prevented. Furthermore, only the second light beam emitted by the probe light beam source 3 reaches the detector 6. The two filters 9a and 9b may both have the same physical characteristics.

The detection of light intensity changes is obtained by way of the two photo-sensitive detectors 5 and 6 whose signals are supplied to an evaluation unit 19 via suitable amplifiers through connecting lines 16a and 16b. The photosensitive first detector 5 measures the light intensity of the excitation light source at the filter 9a. If intensity changes are detected here, the resulting signal intensity changes of the second detector 6 can be corrected by the evaluation unit 19. The second detector 6 measures the actual signal of the thermal lens (T.L.). As the light beam from the excitation light source 4 is chopped in the modulator 17, the second detector receives a T.L. signal which is phase dependent on the modulation frequency. In the evaluation unit, signal evaluation can then be phase-dependent (lock-in technique).

If, for space reasons, the excitation light source 4 and the detector light source 3 can not be arranged close to the sample, it is possible to interpose photo fibers at the locations marked 18 and arrange the light sources 3 and 4 conveniently at a distance.

Below, the adjustment of the sensor according to the invention utilizing the iris diaphragm 10 is described:

Adjustment takes place with closed iris diaphragm 10. If the system is out of proper adjustment by the sample 11, that is, if there is some beam displacement, the two light beams are not exactly aligned with the opening of the aperture diaphragm 12. As a result, the light intensity of the beam from the probe light source 3, which, because of the shading by the iris diaphragm 10, permits passage of only a small part of the light beam as measured at the second detector 6, is relatively small. If the sample 11 is tilted by the adjustable structure 15 normal to the two beams the beam displacement so generated in the sample 11 changes the light intensity measured by the second detector 6. An identical behavior exists for the light beam from the excitation light source 4 whose intensity changes are sensed by a third detector 7 which is also used as, or in place of, a beam stop. If the sample 11 is tilted in such a way that, with closed iris diaphragm 10, the two light beams generate maximum light intensity signals, the light beams are centered on the aperture diaphragm 12 and the sensor is properly adjusted. With a third detector 7 arranged in place of the beam stop, adjustment can be performed automatically. A computer in the evaluation unit 19 evaluates the signals from the two detectors 6 and 7 and moves the sample 11 if necessary. The sample should be tilted at most by an angle of $\alpha=5°$, wherein $\alpha$ is the angle between a normal line extending from the surface of the sample toward the beam divider and the light beam axis.

Figure 2:
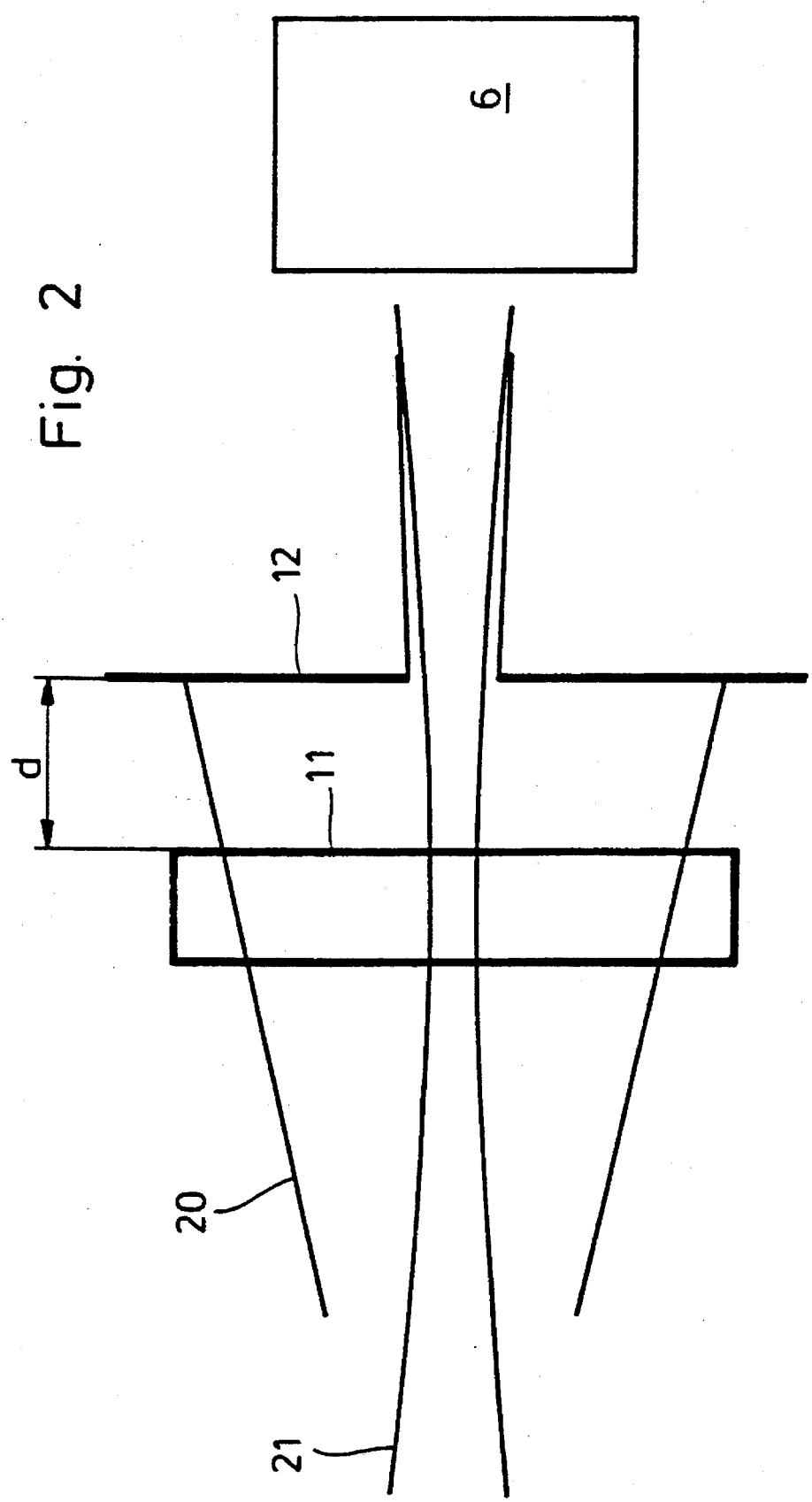
FIG. 2 is a schematic representation of the first (excitation) and the second (probe) light beam and of the Fresnel refraction pattern.

FIG. 2 shows schematically the beam arrangement. Indicated are the sample 11 (for example an aqueous solution in a test cell), the aperture diaphragm 12 and the second detector 6. Reference numeral 21 indicates the first light beam emitted by the excitation light source 4. This light beam is constricted at the sample 11 location. The aperture diaphragm is arranged at a distance d from the sample 11. The opening diameter of the aperture diaphragm is so selected that the first light beam passes through the aperture diaphragm without being inhibited. The second light beam emitted by the probe light source, which is indicated by the numeral 20, is expanded such that its diameter at the sample location is at least 5 times the diameter of the first light beam.

Figure 3:
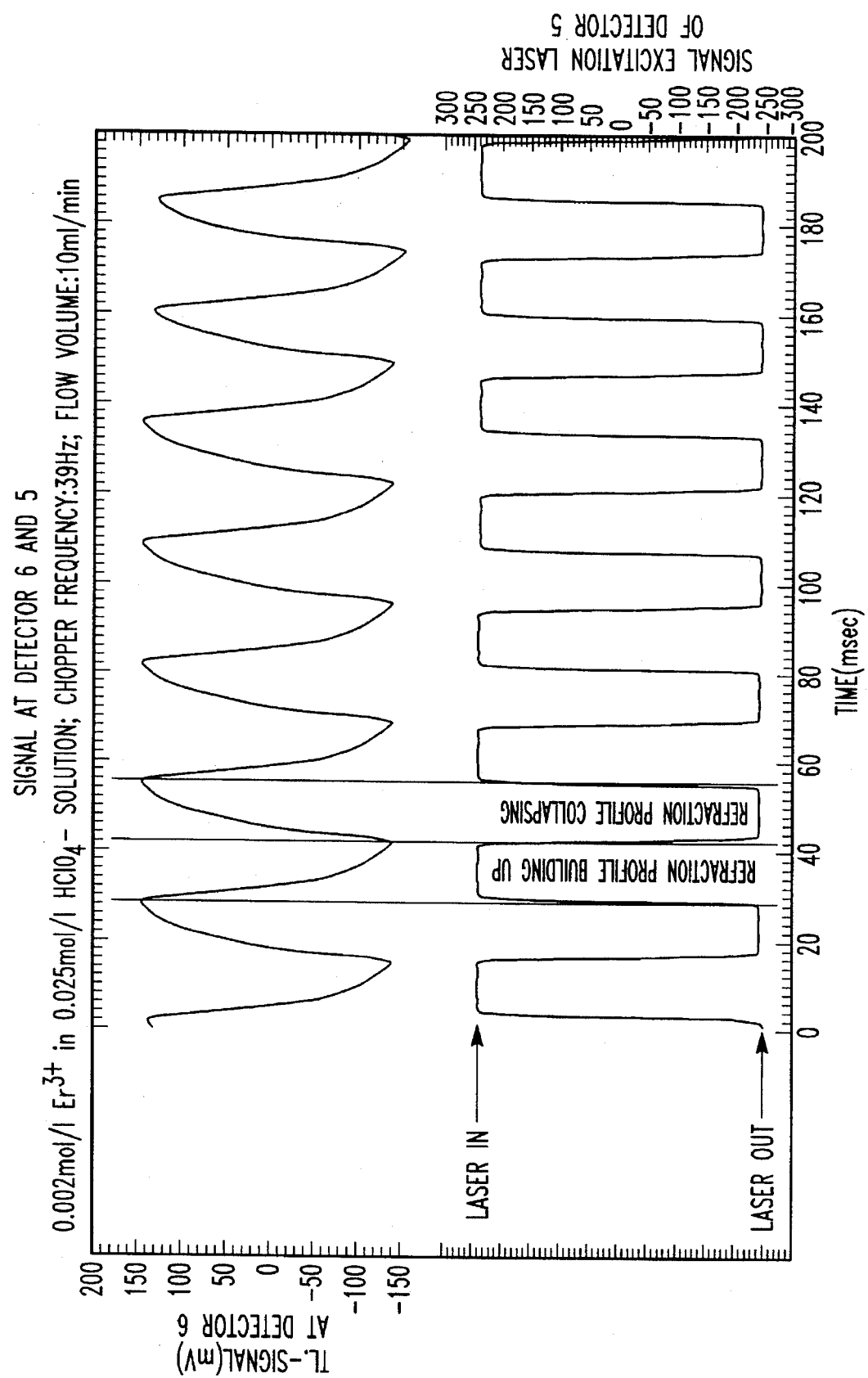
FIG. 3 is a schematic representation of the intensity of the measurement signals over time.

FIG. 3 shows a diagram of the T.L. signal detectable during the photo-thermal measurements. On the abscissa of the diagram the time is given in milliseconds and the detector signals are marked on the ordinate in mV. In the lower portion of the diagram the signal received at the first detector 5 (see FIG. 1) is shown. In the upper part of the diagram the signal measured by the second detector 6 (see FIG. 1) is shown.

Figure 4:
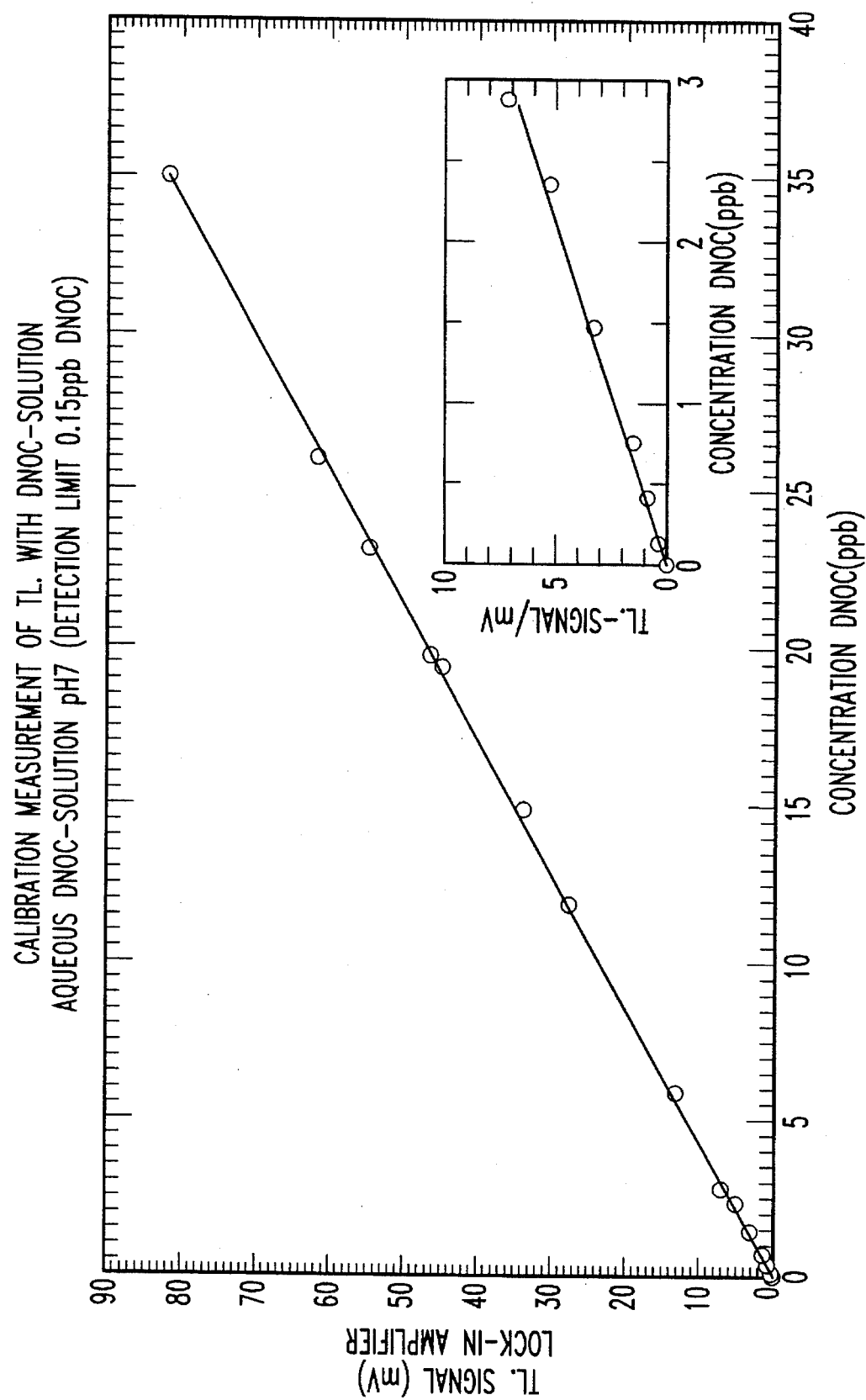
FIG. 4 shows a calibration line for the organic poison compound dinitroorthocresole (DNOC) as determined by the photo-thermal sensor of FIG. 1.

FIG. 4 shows a calibration line which has been measured with the photo-thermal sensor represented in FIG. 1. The samples consisted of a solution of dinitroorthocresole (DNOC) in water. The abscissa gives the concentration of DNOC in ppb and the ordinate indicates the T.L. signal of the second detector 6 (see FIG. 1). As can be seen from the calibration line, the sensor according to the invention is capable of detecting organic compounds in a concentration of only a few ppb.

Figure 5:
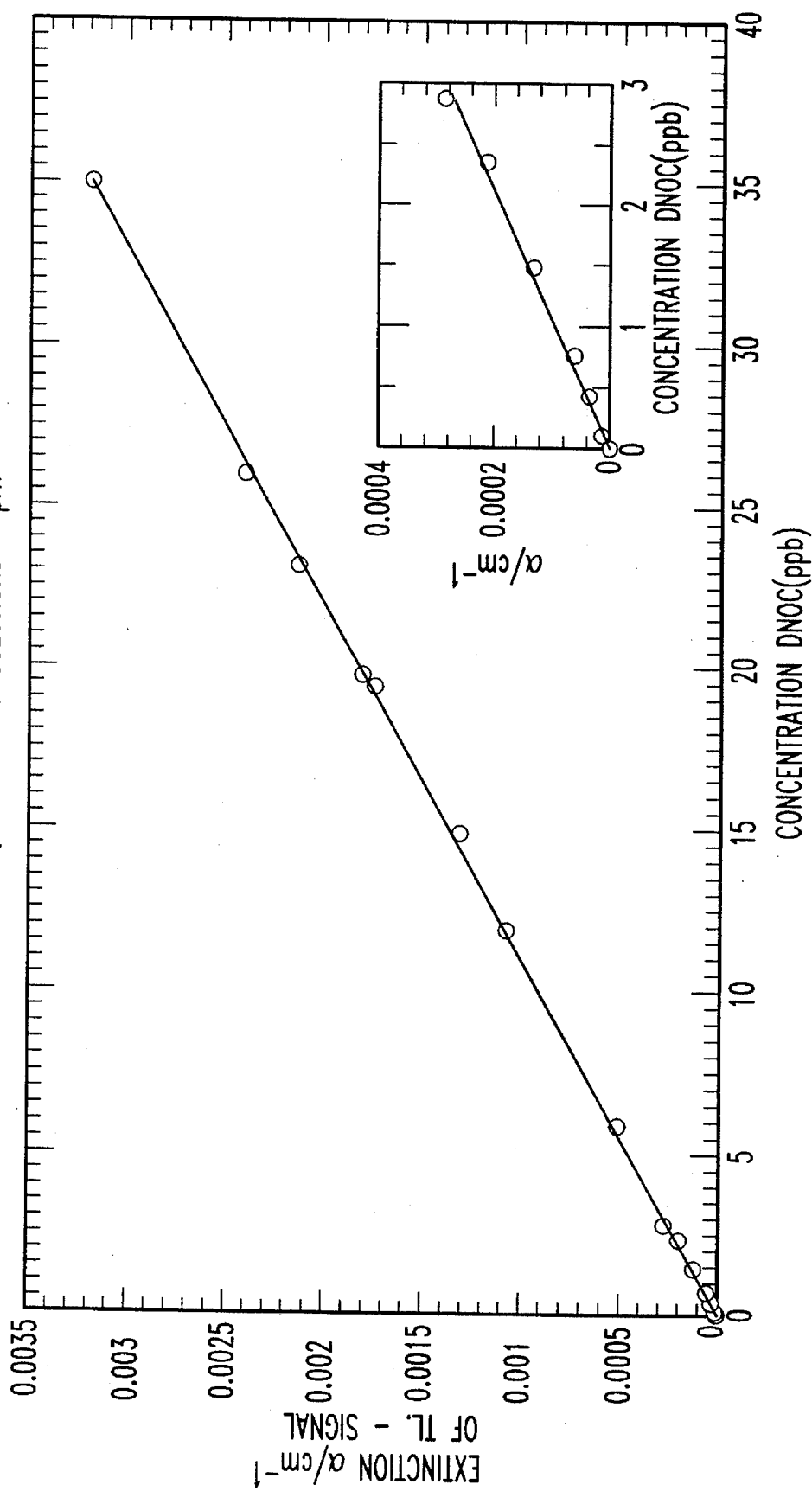
FIG. 5 shows extinction measurements with DNOC.

FIG. 5 shows the results of extinction measurements with DNOC. Again the concentration of DNOC in ppb is given on the abscissa and the extinction in $cm^{-1}$ is given on the ordinate.

What is claimed is:

1. A photo-thermal sensor for determining a concentration of a compound in a sample, comprising:

an excitation light source for generating a first light beam extending along a first light beam path through said sample and having a wave length at which light is well absorbed by the sample compound to be determined, said sample being disposed at a predetermined location, a modulator disposed in said first light beam path, an optical lens system arranged so as to be disposed in said first light beam path after said modulator such that said first light beam is constricted where it passes through of said sample, a probe light source for generating a second light beam of a coherent light extending along a second path, said probe light source being so arranged that said second light beam extends at a right angle to said first light beam and intersects said first light beam at a predetermined point, a lens arranged in said second light beam path for expanding said second light beam to such a degree that said second light beam has a radius at the sample location which is at least five times as large as the radius of said first light beam, a beam divider having opposite sides and being arranged at the point of intersection of said first and second light beams such that the first light beam emitted from the excitation light source, after passing through the modulator and the optical lens system, is deflected at one side of the beam divider and the second beam emitted from the probe light source reaches the opposite side of said beam divider and is transmitted through said beam divider whereby a first part of said first light beam as well as part of said second light beam coincide on said sample, a first photo-sensitive detector arranged in the first light beam path behind said sample for receiving a second part of said first light beam after its passage through said sample, a diaphragm arranged in the first beam path immediately after said sample and a second beam divider arranged in said first beam path after said diaphragm for partially reflecting the first light beam, a second photo sensitive detector arranged in a part of said first beam path after said first beam divider for receiving said part of said first light beam, which passes through said first beam divider and an evaluation unit in communication with said first and second photo-sensitive detectors for determining and indicating the concentration of the compound to be determined in said sample.

2. A photo-thermal sensor according to claim 1, wherein said optical lens system includes an achromatic lens.

3. A photo-thermal sensor according to claim 1, wherein said beam divider is a long or short wave pass filter.

4. A photo-thermal sensor according to claim 1, wherein an iris diaphragm is arranged in said first beam path between said beam divider and said sample.

5. A photo-thermal sensor according to claim 1, wherein said diaphragm arranged after said sample is an aperture diaphragm.

6. A photo-thermal sensor according to claim 1, wherein said second beam divider is a long or short wave pass filter and a beam stop is provided to receive the light deflected by said beam divider.

7. A photo-thermal sensor according to claim 6, wherein said beam stop includes a third photo sensitive detector.

8. A photo-thermal sensor according to claim 1, wherein, during the determination of the concentration of a compound of a solution received in a cell serving as said sample, the modulator has a frequency of 4 to 6 Hz.

9. A photo-thermal sensor according to claim 1, wherein, for the determination of the concentration of a compound contained in a solution passing through a flow tube serving as a sample, the modulator has a frequency of 40 to 60 Hz.

10. A photo-thermal sensor according to claim 1, wherein, for the determination of the concentration of a compound contained in a solid body serving as a sample, the modulator has a frequency of about 3000 Hz.

11. A photo-thermal sensor according to claim 1, wherein, at the sample location, the radius of said second light beam is up to 50 times the radius of said first light beam.

* * * * *